US009989469B2

(12) United States Patent
Fukuda et al.

(10) Patent No.: US 9,989,469 B2
(45) Date of Patent: Jun. 5, 2018

(54) SAMPLE ANALYZER AND METHOD FOR CONTROLLING A SAMPLE ANALYZER

(71) Applicant: SYSMEX CORPORATION, Kobe-shi, Hyogo (JP)

(72) Inventors: Masakazu Fukuda, Kobe (JP); Masamichi Tanaka, Kobe (JP); Rumi Takata, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 1184 days.

(21) Appl. No.: 13/853,619

(22) Filed: Mar. 29, 2013

(65) Prior Publication Data

US 2013/0260415 A1 Oct. 3, 2013

(30) Foreign Application Priority Data

Mar. 30, 2012 (JP) ................ 2012-079927

(51) Int. Cl.
*G01N 35/10* (2006.01)
*G01N 21/64* (2006.01)
*G01N 35/00* (2006.01)

(52) U.S. Cl.
CPC ..... *G01N 21/6486* (2013.01); *G01N 35/1004* (2013.01); *G01N 35/1095* (2013.01)

(58) Field of Classification Search
CPC ........... G01N 21/6486; G01N 35/00029; B01J 19/0006; B01J 2400/0406

USPC .................. 422/50, 62, 63; 435/34
See application file for complete search history.

(56) References Cited

U.S. PATENT DOCUMENTS

| 5,365,559 A * | 11/1994 | Hsueh ................ G01N 15/0205 324/71.4 |
| 2008/0187990 A1 | 8/2008 | Nagai et al. |
| 2009/0035182 A1 | 2/2009 | Soma et al. |

FOREIGN PATENT DOCUMENTS

| CN | 101236194 A | 8/2008 |
| CN | 101358986 A | 2/2009 |
| JP | H05-209822 A | 8/1993 |
| JP | 2001-242181 A | 9/2001 |
| JP | 2003-232797 A | 8/2003 |
| JP | 2008-209383 A | 9/2008 |
| JP | 2010-169455 A | 8/2010 |

* cited by examiner

*Primary Examiner* — Christine T Mui
(74) *Attorney, Agent, or Firm* — Metrolexis Law Group, PLLC

(57) ABSTRACT

Disclosed is a sample analyzer comprising: a sample measuring section including a detecting section for detecting a component contained in a sample and a flow path for feeding the sample to the detecting section; and a control section. The control section is programmed to automatically control the sample measuring section to flow a sample blank free of particles to the detecting section and detect a component contained in the sample blank to check a background of the detection after the sample measuring section performs washing of the flow path.

18 Claims, 11 Drawing Sheets

SAMPLE ANALYZER AND METHOD FOR CONTROLLING A SAMPLE ANALYZER

FIELD OF THE INVENTION

The present invention relates to a sample analyzer capable of measuring a clinical sample such as cerebrospinal fluid, pleural effusion, and the like as a sample collected from a patient. The present invention also relates to a method for controlling such a sample analyzer by a computer.

BACKGROUND

Generally, in the sample analyzer for aspirating the sample such as blood, and flowing the aspirated sample through a flow path to a flow cell and measuring the same, the flow path used for the measurement is cleaned after the measurement to prevent the component such as blood cells from remaining on the flow path, and influencing the measurement result of the next sample (carry over). In particular, normally, the body fluid such as cerebrospinal fluid, pleural effusion, and the like barely contain cells, and thus the measurement result greatly fluctuates if the component is remaining in the flow path even slightly when measuring such body fluid. Thus, when measuring body fluid it is very important to reduce the carry-over. The technique for reducing the carry-over of when measuring the body fluid is proposed by U.S. Patent Application Publication No. 2008/0187990.

The sample analyzer displays a message urging the blank check measurement on a screen to notify that the measurement result of the next body fluid sample may be influenced if the measurement result of body fluid prior measured is greater than or equal to a predetermined value. When the user instructs the execution of the blank check measurement according to such message, the measurement is carried out using a sample blank that does not contain the body fluid, and whether or not the cells of a predetermined value or greater is counted in the background is determined.

In the sample analyzer described in U.S. Patent Application Publication No. 2008/0187990, the necessity of the blank check measurement is determined in accordance with whether or not the measurement result of prior measured body fluid is greater than or equal to a predetermined value. This is because the flow path is assumed to be sufficiently washed and background noise is assumed to be sufficiently reduced by the washing after the measurement if the measurement result is smaller than the predetermined value.

However, some careful users may perform the blank check measurement each time after the sample measurement and following washing is completed irrespective of the measurement result of the sample measured prior in order to check that the flow path is sufficiently washed. If it is confirmed that the flow path is sufficiently cleaned, next body fluid sample is measured. In order to perform such operation, the operation to instruct the blank check measurement is required each time after the measurement of the body fluid sample.

SUMMARY OF THE PRESENT INVENTION

A first aspect of the present invention is a sample analyzer comprising: a sample measuring section including a detecting section for detecting a component contained in a sample and a flow path for feeding the sample to the detecting section; and a control section, wherein when measuring the sample, the sample measuring section feeds the sample to the detecting section through the flow path, detects the component contained in the sample with the detecting section, and then flows washing fluid to the flow path to perform washing of the flow path, and after the sample measuring section performs the washing, the control section is programmed to automatically control the sample measuring section to flow a sample blank to the detecting section and detect a component contained in the sample blank to check a background of the detection.

A second aspect of the present invention is a sample analyzer comprising: a sample measuring section including a flow path for feeding a sample, and a detecting section for detecting a component contained in the sample fed through the flow path; and a control section for controlling the sample measuring section based on a mode selected from a first mode for measuring a first type of sample and a second mode for measuring a second type of sample, the mode being selected by a user, wherein when the first mode or the second modes is set, the sample measuring section causes the flow path to feed the sample toward the detecting section and causes the detecting section to detect the component contained in the sample, and thereafter, causes the flow path to flow washing fluid, when the second mode is set, the control section causes the sample measuring section to automatically perform a background check for checking effect of the washing after the washing fluid is flown to the flow path, and when the first mode is set, the control section permits the measurement of a next sample with skipping the background check.

A third aspect of the present invention is a method for controlling a sample analyzer by a computer, the method comprising the steps of: (a) flowing a sample to a detecting section of the sample analyzer through a flow path; (b) detecting a component contained in the sample with the detecting section; (c) flowing washing fluid to the flow path and the detecting section; (d) flowing a sample blank to the detecting section through the flow path; (e) detecting a component contained in the sample blank with the detecting section; and (f) outputting an alert indicating that a risk of carry-over is high if an amount of component detected in the steps (c) exceeds a predetermined threshold value, wherein the computer is programmed to automatically perform the steps (d), (e), and (f) after the step (c) is completed.

EMBODIMENTS

The embodiments of the present invention will be described with reference to the appended drawings.

Figure 1:
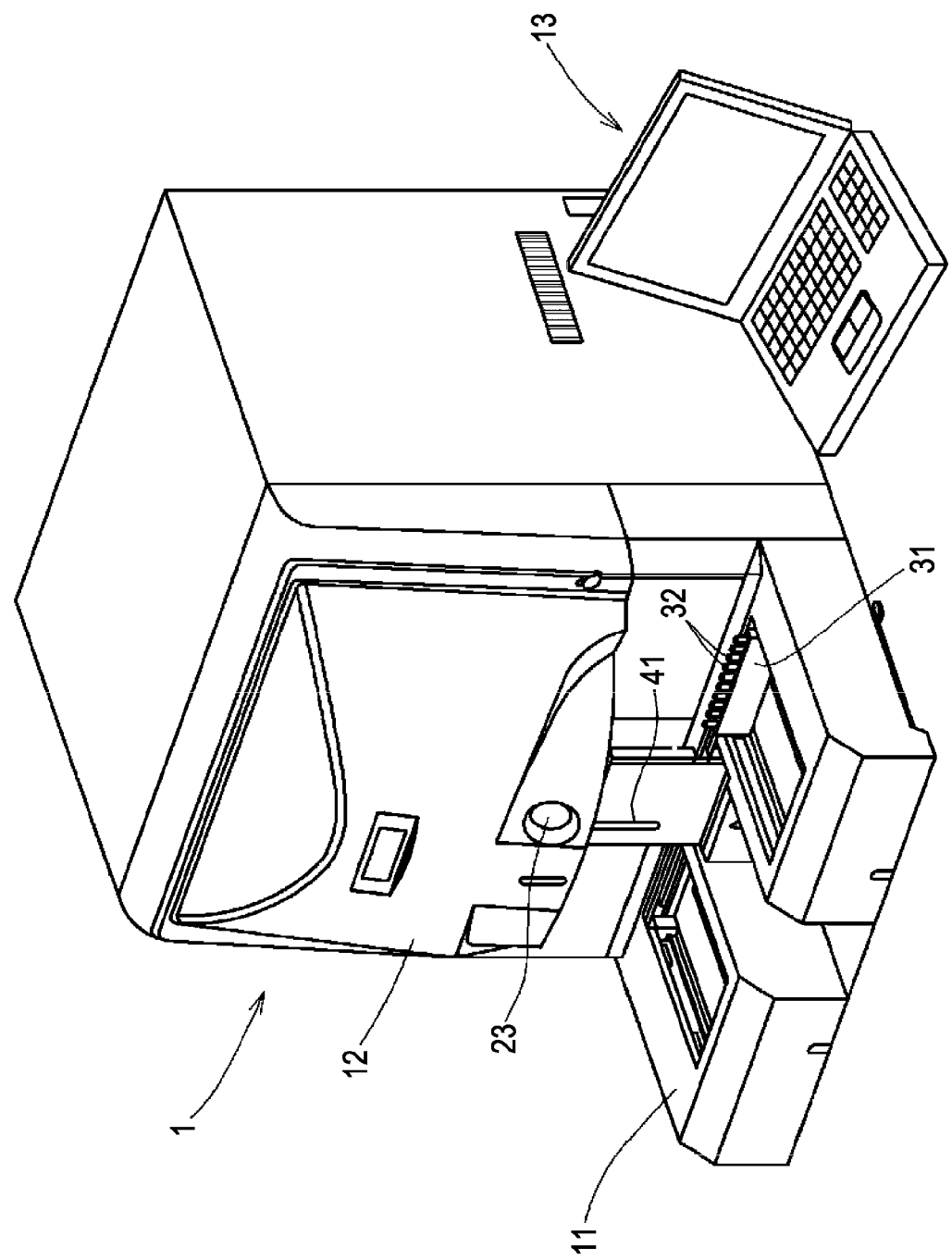
FIG. 1 is a perspective view showing a sample analyzer according to one embodiment of the present invention.

FIG. 1 is a perspective view showing a sample analyzer according to one embodiment of the present invention. As shown in FIG. 1, a sample analyzer 1 illustrated in the present embodiment is a urine analyzer. The sample analyzer 1 mainly includes a transporting section 11, a measuring section (sample measuring section) 12 for performing measurement of the sample, and a system control section 13, connected to the measuring section, for performing analysis of the measurement result. The sample analyzer 1 aspirates urine serving as a sample from a test tube 32 accommodated in a rack 31 transferred by the transporting section 11, detects formed elements such as red blood cells and white blood cells, and particles such as bacteria from the urine, and analyzes the detection result.

The sample analyzer 1 can measure not only urine but also body fluid. In the present specification, the term "body fluid" refers to a body cavity fluid present in the body cavity. Specifically, the body fluid refers to the cerebrospinal fluid (CSF: fluid filled in ventricular chamber and subarachnoid cavity), pleural effusion (PE: fluid accumulated in pleural cavity), ascitic fluid (fluid accumulated in peritoneal cavity), pericardial fluid (fluid accumulated in pericardial cavity), joint fluid (bone fluid: fluid present in joint, synovial sac, and tendon sheath), and the like. The dialysis fluid of peritoneal dialysis (CAPD), intra-abdominal washing fluid, and the like are also a type of body fluid.

Figure 2:
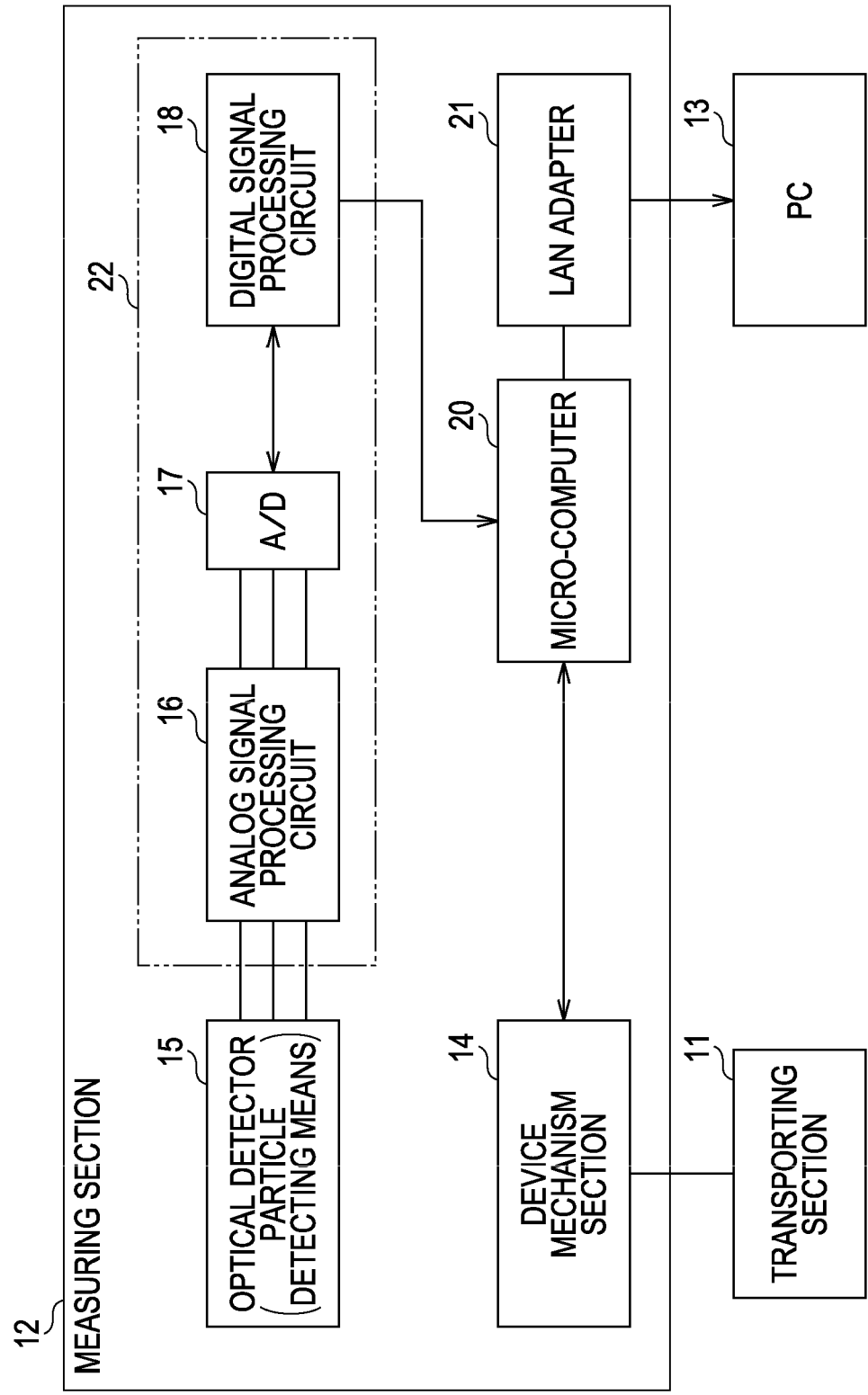
FIG. 2 is a block diagram showing an overall configuration of the sample analyzer.

FIG. 2 is a block diagram showing an overall configuration of the sample analyzer 1. As shown in FIG. 2, the measuring section 12 of the sample analyzer 1 includes a device mechanism section 14 for aspirating and quantifying urine or body fluid; an optical detector 15 for detecting particles in the sample quantified by the device mechanism section 14, and outputting an electric signal corresponding to the characteristics of the detected particles to an analog signal processing circuit 16, the analog signal processing circuit 16 for performing amplification and filter processing of the output from the optical detector 15, an A/D converter 17 for converting the output of the analog signal processing circuit 16 to a digital signal, a digital signal processing circuit 18 for performing a predetermined processing on the digital signal, a micro-computer 20 connected to the digital signal processing circuit 18, and a LAN adapter 21 connected to the micro-computer 20.

A personal computer (PC) configuring the system control section 13 is LAN connected to the measuring section 12 through the LAN adapter 21, which personal computer 13 performs analysis of the data acquired by the measuring section 12. The analog signal processing circuit 16, the A/D converter 17, and the digital signal processing circuit 18 configure a signal processing unit 22 for processing the electric signal output by the optical detector 5.

Figure 3:
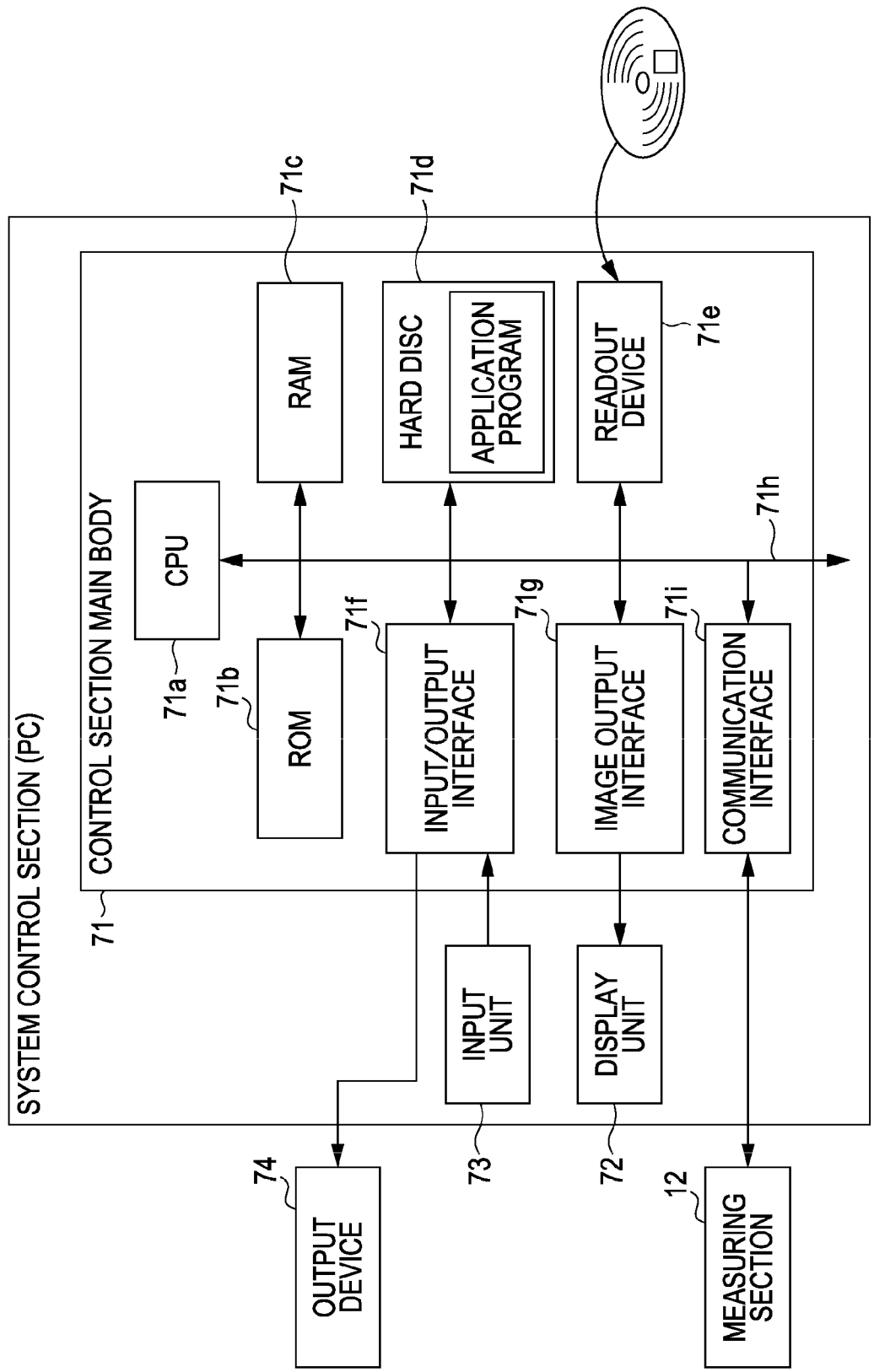
FIG. 3 is a block diagram of a system control section.

FIG. 3 is a block diagram of the system control section 13. As shown in FIG. 3, the system control section 13 includes a personal computer, and is mainly configured by a control section main body (controller) 71 for performing control of the device mechanism section 14, a display unit 72, an input unit 73, and an output device 74. The control section main body 71 is mainly configured by a CPU 71a, a ROM 71b, a RAM 71c, a hard disc 71d, a readout device 71e, an input/output interface 71f, image output interface 71g, and a communication interface 71i. These are communicably connected by a bus 71h.

Forward scattered light signal, side scattered light signal, and fluorescence signal processed by the signal processing unit 22 is input to the system control section 13 through the LAN adapter 21 by the micro-computer 20. In the system control section 13, the particles in the sample are classified into red blood cells, white blood cells, epidermal cells, casts, bacteria, and others based on the forward scattered light signal, the side scattered light signal, and the fluorescence signal. The system control section 13 creates a scattergram or a histogram for analyzing the particles. The scattergram or histogram is displayed on the display unit 72. The system control section 13 has a function serving as a mode setting section capable of selectively setting a first mode, in which a urine sample serving as a first type of sample is measured, and a second mode, in which a body fluid sample serving as a second type of sample is measured. In the present embodiment, the user operates a mode switching button 72c (see FIG. 10A) displayed on the display unit 72 of the system control section 13 to instruct the system control section 13 to the switch from the first mode to the second mode, and to switch from the second mode to the first mode.

Figure 4:
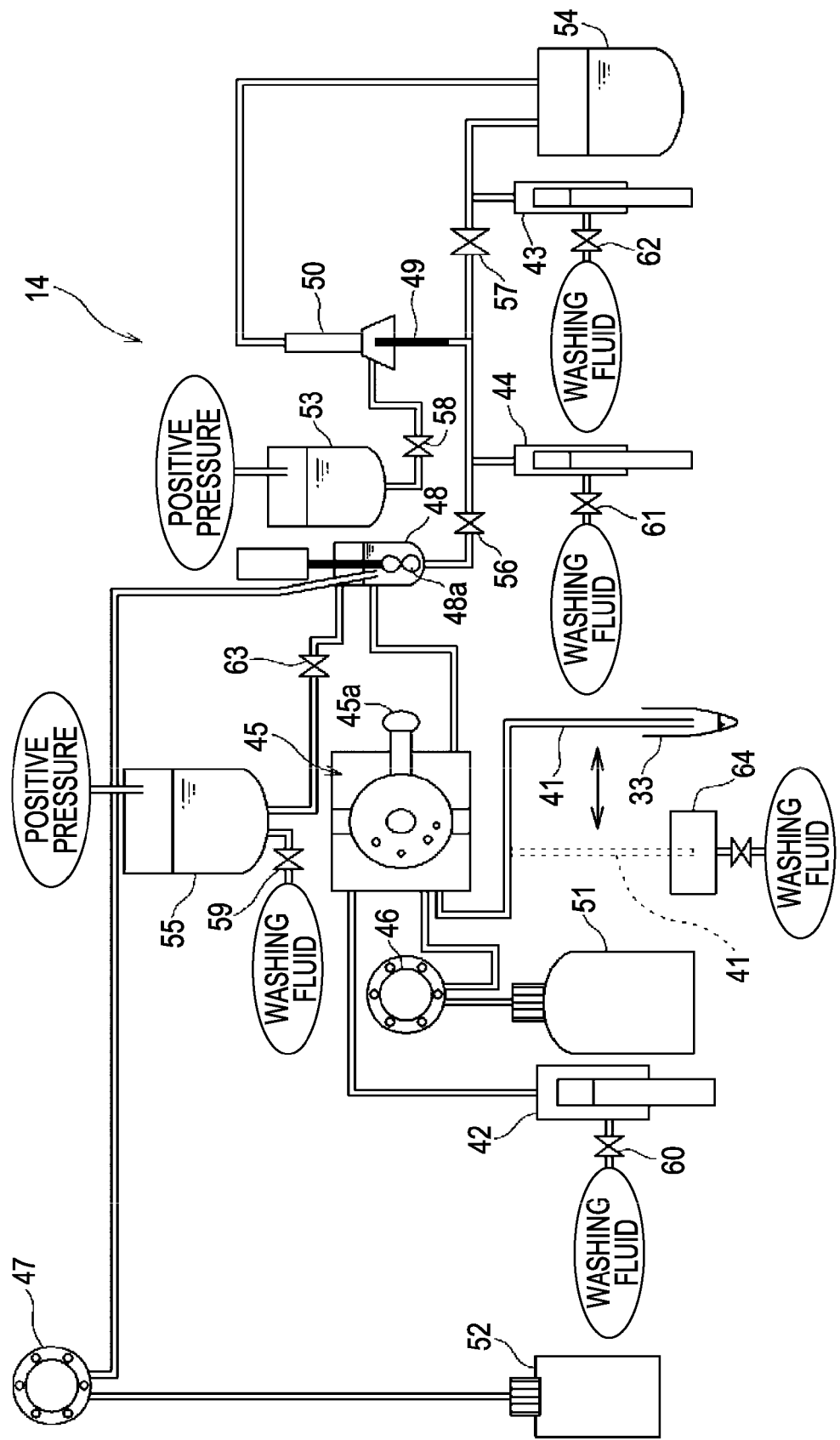
FIG. 4 is a fluid circuit diagram of a device mechanism section in a measuring section.

FIG. 4 is a fluid circuit diagram of the device mechanism section 14 in the measuring section 12. As shown in FIG. 4, the device mechanism section 14 includes an aspirating pipette 41, syringe pumps 42 to 44, a sampling valve 45, diaphragm pumps 46, 47, a reaction chamber 48, a jet nozzle 49, a flow cell 50, a diluting solution container 51, a stain fluid container 52, a sheath fluid container 53, a waste chamber 54, a washing fluid container 55, valves 56 to 63, and a washing unit 64.

The aspirating pipette 41 aspirates with the syringe pump 42 the sample from the micro-tube 33 containing the body fluid sample or the test tube 32 (see FIG. 1) containing the urine, and feeds the aspirated sample to the sampling valve 45. The sampling valve 45 is used as a quantifying mechanism. The sampling valve 45 quantifies the sample under operation by a switching arm 45a. The quantified sample is dispensed into the reaction chamber 48 with the diluting solution flown from the diluting solution container 51 by the diaphragm pump 46. The stain fluid is also dispensed into the reaction chamber 48 from the stain fluid container 52 by the diaphragm pump 47. The reaction chamber 48 includes a stirring blade 48a. The stain fluid and the sample are mixed by operating the stirring blade 48a, and the particles contained in the stain are fluorescent stained.

The valve 56 and the valve 57 are opened. The sample mixed with the stain fluid is flown from the reaction chamber 48 to be charged in the flow path between the valve 56 and the valve 57 by applying negative pressure from the syringe pump 43 to the flow path. The valves 56, 57 are then closed. The sample charged between the valves 56, 57 is pushed out toward the jet nozzle 49 by applying positive pressure from the syringe pump 44 to the flow path and discharged from the jet nozzle 49 to the flow cell 50. At the same time as discharging, the sheath fluid is pushed out by the positive pressure from the sheath fluid container 53 by opening the valve 58, and the sample forms a narrow flow (sheath flow) surrounded by the sheath fluid in the flow cell 50. The cells in the sample are lined one by one in a line and flow through the center of the flow cell 50. The sample and the sheath fluid that passed through the flow cell 50 are discharged to the waste chamber 54.

The cell row of the sheath flow in the flow cell 50 is irradiated with laser light. The scattered light, which reflects the size of the cell, and the fluorescence, which reflects the information of the cell nucleus, are detected by the optical detector 15. Such detected signals are converted to electric signals, and transmitted to the system control section 13 (see FIG. 2) for analysis. In the system control section 13, the particles in the specimen are classified to white blood cells, red blood cells, bacteria, and the like, based on the individual signal of each cell. Respective particles are counted, and the counted result is displayed on the display unit 72 (see FIG. 3). The system control section 13 creates scattergram or histogram based on the received signal, and displays the scattergram or the histogram on the display unit 72 with the counted result.

Figure 11:
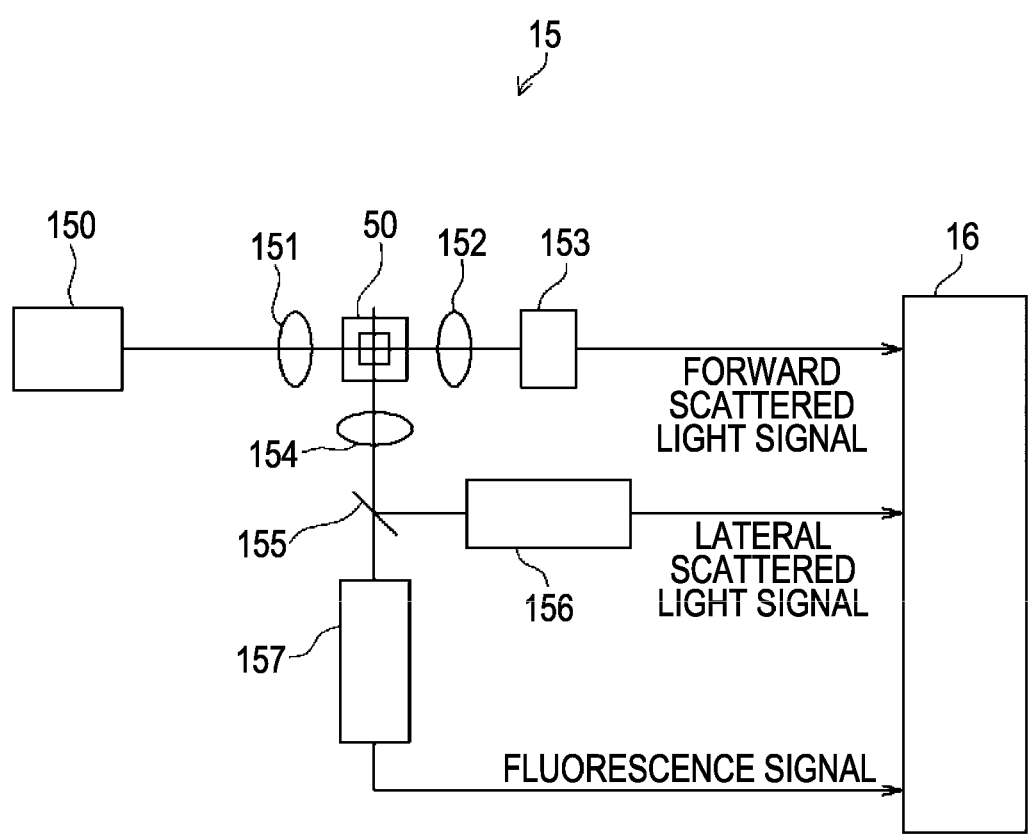
FIG. 11 is an explanatory view showing a configuration of an optical detector.

FIG. 11 is an explanatory view showing a configuration of the optical detector 15. The optical detector 15 and the flow cell 50 configure a so-called flow cytometer. A light source 150 radiates laser light toward the flow cell 50. A condenser lens 151 collects the laser light radiated from the light source 150 at the flow cell 50. A light collecting lens 152 collects the forward scattered light emitted from the particles at a photodiode 153. A light collecting lens 154 collects the side scattered light and the fluorescence emitted from the particles at photo-multiplier tubes 156 and 157 via a dichroic mirror 155. The dichroic mirror 155 reflects the side scattered light to the photo-multiplier tube 156, and transmits the fluorescence toward the photo-multiplier tube 157. The photodiode 153, the photo-multiplier tube 156, and the photo-multiplier tube 157 convert the received light to an electric signal corresponding to the intensity of light, and respectively output a forward scattered light signal (FSC), the side scattered light signal (SSC), and the fluorescence signal (FL). Output signals are amplified by a pre-amplifier (not shown), and then input to the analog processing circuit 16. The particles flowing through the flow cell 50 are detected based on such outputs.

In the present embodiment, flow path through which a sample passes, such as the aspirating pipette 41, the sampling valve 45, and the reaction chamber 48 are washed after the sample passes therethrough. The washing of the flow path includes first half and second half. The washing of flow path is performed at a timing the measurement of the sample is not inhibited. The first half of the washing (this washing is hereinafter referred to as "washing A") is initiated when the stain fluid in the stain fluid container 52 is dispensed to the reaction chamber 48. In the washing A, flow path used for the aspiration and the quantification of the sample is washed. Specifically, the aspirating pipette 41 is moved to a position shown with a broken line in FIG. 4, and inserted into the washing unit 64. The switching arm 45a of the sampling valve 45 is operated to be the original position. The valve 59 and the valve 60 are opened. Washing fluid in the washing fluid container 55 is passed through the syringe pump 42, the sampling valve 45, and the aspirating pipette 41 and discharged into the washing unit 64 by the positive pressure. The interior of the aspirating pipette 41 is thereby washed. The washing unit 64 can wash the outer periphery of the aspirating pipette 41 by discharging the washing fluid to the inserted aspirating pipette 41. The syringe pump 42 and the aspirating pipette 41 are returned to the original position so that the next sample can be aspirated after the washing.

The second half of the washing (this washing is hereinafter referred to as "washing B") is initiated when the analysis of the system controller 13 is started based on the electric signal transmitted from the optical detector 15. In washing B, flow path used to discharge the sample to the waste chamber 54 is washed. Specifically, the valve 59 and the valve 61 are opened while the valves 56, 57 and 62 are closed. Thus positive pressure is applied to the washing fluid container 55 and then washing fluid therein are thus passed through the syringe pump 44, flow path between the valves 56, 57, the jet nozzle 49, and the flow cell 50 and discharged to the waste chamber 54. After a few seconds, the valve 57 is opened so that the washing fluid remaining in the jet nozzle 49 and flow path between the valves 56, 57 is passed through the valve 57 and discharged 25 to the waste chamber 54.

The valve 63 positioned between the washing fluid container 55 and the reaction chamber 48 is opened. Then washing fluid is flown to the reaction chamber 48. The stirring blade 48a is actuated to stir the washing fluid in the reaction chamber 48. After the washing, the valves 56, 57 are opened so that the washing fluid in the reaction chamber 48 is passed through the valves 56, 57 and discharged to the waste chamber 54. Washing of flow path from the reaction chamber 48 to the waste chamber 54 is carried out in such manner.

The device mechanism section 14 thus has a function of washing flow path flowing a sample such as urine or body fluid.

The operation of the sample analyzer 1 according to the present embodiment will now be described with reference to FIG. 5 to FIG. 9.

Figure 5:
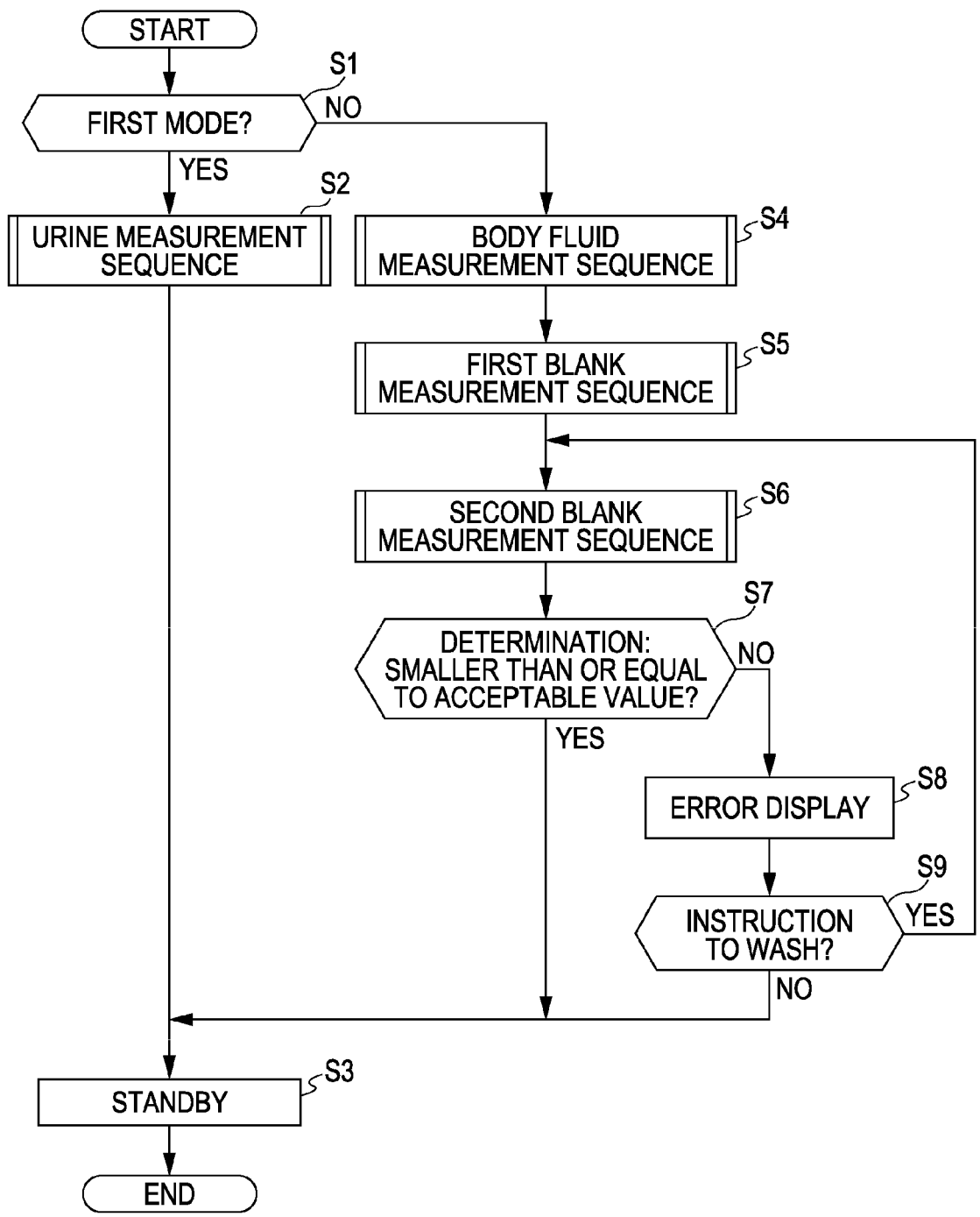
FIG. 5 is a flowchart showing a processing procedure of the sample analyzer.

FIG. 5 is a flowchart showing an operation of when the sample analyzer 1 accepts an instruction to start the measurement from the operator. When the operator pushes a measurement start button 23 (see FIG. 1), the process starts. As shown in FIG. 5, the system control section 13 first determines which one of the modes, the first mode for measuring urine sample or the second mode for measuring body fluid sample, is set (step S1). If the first mode is set, the system control section 13 executes a urine measurement sequence for measuring a urine sample (step S2).

Figure 6:
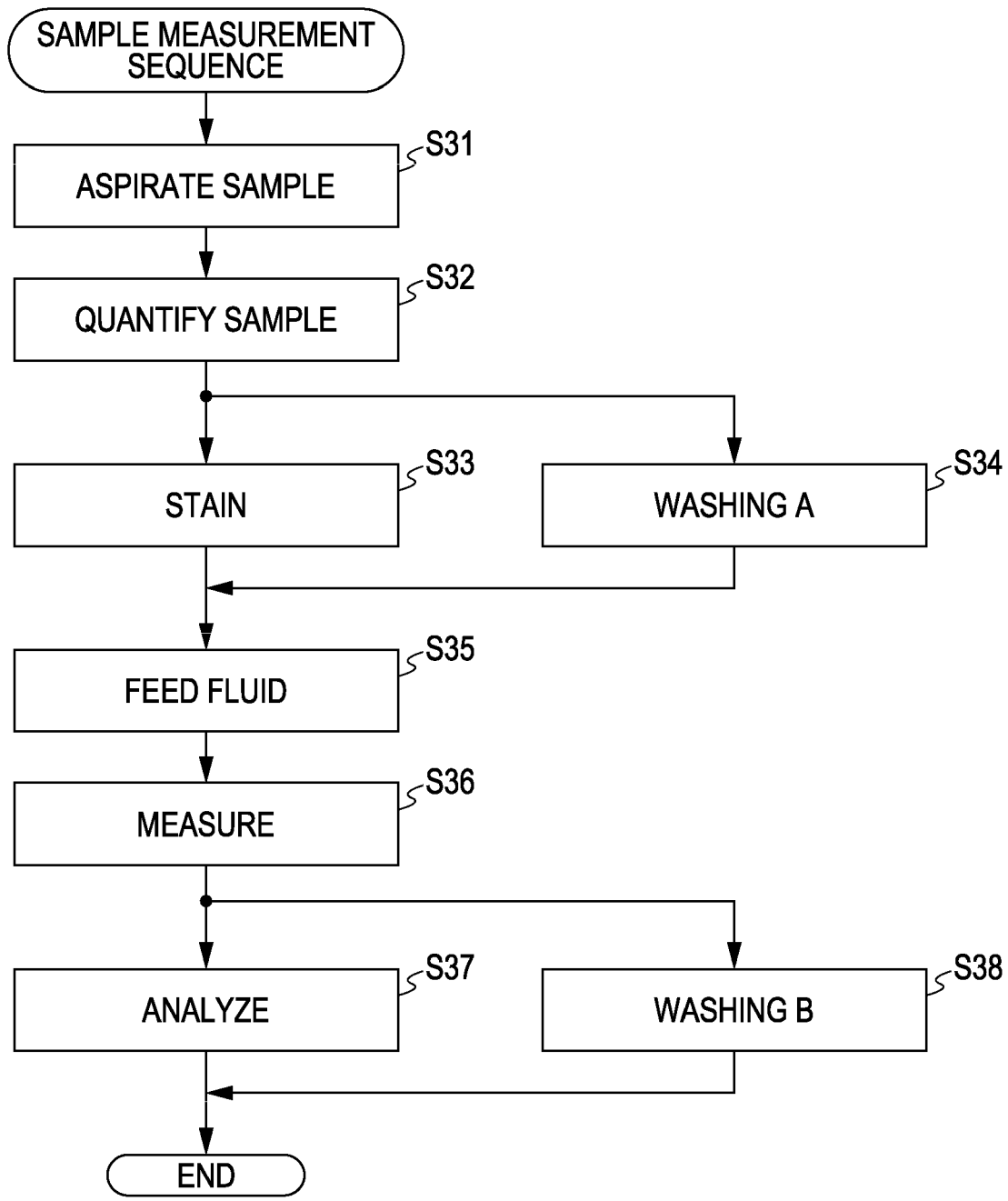
FIG. 6 is a flowchart showing a processing procedure of a sample measurement sequence.

FIG. 6 is a flowchart showing a processing of the sample measurement sequence. Note that, the sample measurement sequence of FIG. 6 is a sequence commonly performed in both of the urine measurement sequence in step S2 and the body fluid measurement sequence in step S4. As shown in FIG. 4 and FIG. 6, the measuring section 12 transports the rack 31 by the transporting section 11, and starts the aspiration of the urine sample in the test tube 32 with the aspirating pipette 41 (step S31). The aspirated urine sample is quantified by the sampling valve 45, and then dispensed into the reaction chamber 48 with the diluting solution (step S32). The stain fluid is dispensed into the reaction chamber 48, and the mixture is stirred with the stirring blade 48a so that the urine sample is fluorescence stained (step S33).

At the same time as the start of staining of the urine sample by the stain fluid, the washing A for washing flow path used in steps S31 and S32 is started. In other words, the washing fluid in the washing fluid container 55 is passed through the syringe pump 42, the sampling valve 45, and the aspirating pipette 41, and then discharged (step S34). After the washing A and the staining of the urine sample are finished, the stained urine sample is flown from the reaction chamber 48 to be charged in the flow path between the valve 56 and the valve 57 (step S35).

The urine sample charged between the valves 56, 57 is then measured. In this measurement, the urine sample charged between the valves 56, 57 is pushed out by the syringe pump 44, and discharged from the jet nozzle 49 into the flow cell 50. The sheath fluid is pushed out at the same time as the discharging, and the sheath flow of the urine sample formed in the flow cell 50 is irradiated with the laser light emitted from the light source 150 (FIG. 11), so that the optical detector 15 detects particles in the urine. The detection signal is then converted to an electric signal and transmitted to the system control section 13 (step S36).

In the system control section 13, the electric signal is analyzed (step S37). The analysis result of counting the white blood cells, the red blood cells, and the bacteria, as well as the scattergram and the histogram created in accordance with the electric signal are displayed on the display unit 72. At the same time as the start of analysis by the system control section 13, the washing B for washing the flow path used in the steps S35, S36 in the device mechanism section 14 is started. In other words, the washing fluid in the washing fluid container 55 is passed through the syringe pump 44, between the valves 56, 57, the jet nozzle 49, and the flow cell 50, and discharged into the waste chamber 54. The washing of the reaction chamber 48 is carried out by stirring the washing fluid discharged from the washing fluid container 55 to the reaction chamber 48 with the stirring blade 48a (step S38). As described above, the washing A and the washing B are carried out in parallel with the measurement and the analysis of the urine sample, whereby the time required from the start of measurement of the urine sample to the completion of the washing can be reduced and the throughput can be enhanced.

Figure 10A:
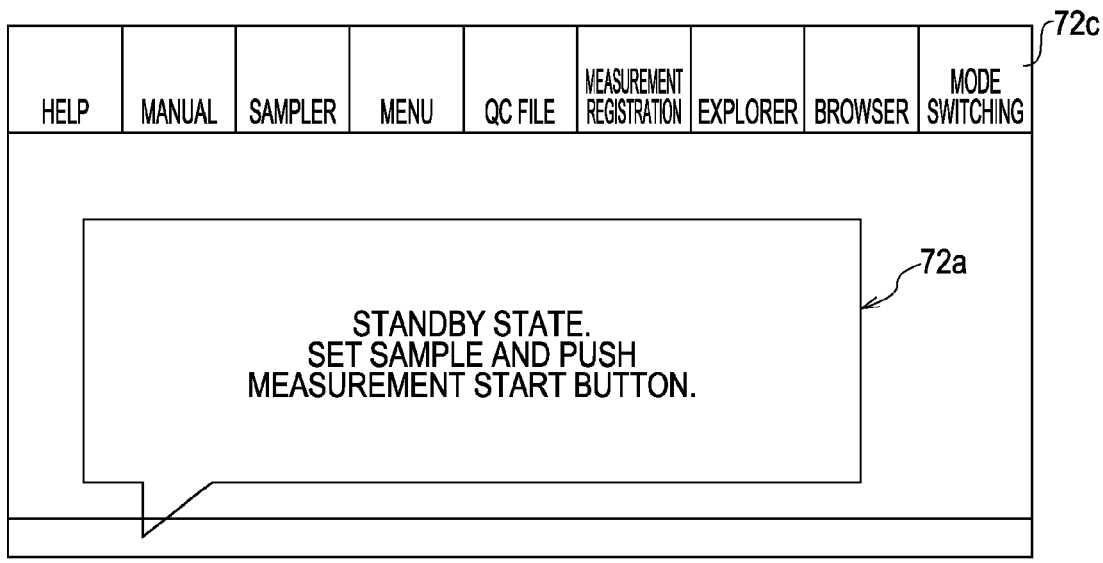
FIG. 10A is an illustrative view of a standby screen displayed on a display unit.

Returning back to FIG. 5, after the urine measurement sequence of measuring the urine sample in step S2 is finished, a standby state in which the next urine sample can be measured is achieved (step S3). In the standby state, a message 72a indicating the standby state is displayed on the display unit 72 of the system control section 13, as shown in FIG. 10A. The notification of standby is not limited to a form of message. The notification may be other characters, figures, or colors as long as it enables the user to understand that the standby state is achieved.

If the second mode is set in step S1, on the other hand, the system control section 13 executes a body fluid measurement sequence (step S4) of measuring the body fluid sample.

The operation of measuring the body fluid sample will now be described. If the second mode is set, the aspirating pipette 41 is arranged in a projecting manner in front of the device, as shown in FIG. 1. The user holds the micro-tube 33 containing the body fluid and lifts up the micro-tube 33 from under with respect to the aspirating pipette 41 to insert the aspirating pipette 41 into the micro-tube 33, and pushes the measurement start button 23 in this state. The body fluid measurement sequence is thereby started, and the body fluid sample is aspirated from the micro-tube 33 by the aspirating pipette 41.

The body fluid measurement sequence of measuring the body fluid sample is similar to the urine measurement sequence (steps S31 to S38) of measuring the urine sample, described above, other than that the body fluid sample is aspirated from the micro-tube 33 in the sample aspiration (step S31) of FIG. 6, and thus the detailed description thereof will be omitted.

When the body fluid measurement sequence of measuring the body fluid sample is carried out, the blank measurement involving washing of the flow path is automatically executed two times. In other words, a first blank measurement sequence (step S5) and a second blank measurement sequence (step S6) are sequentially executed automatically.

The blank measurement is a measurement that uses a sample blank that does not contain cells in place of the sample to check a background. In the present embodiment, the washing fluid in the washing fluid container 55 is measured as the sample blank. If a great amount of cells is detected as a result of the blank measurement, this means that the cells remain in the flow path and that the washing of the flow path is not sufficient. Although the washing fluid is used for the sample blank in the present embodiment, various kinds of fluids may be used as the sample blank, for example, the diluting solution or water as long as the fluid does not contain cells.

Figure 7:
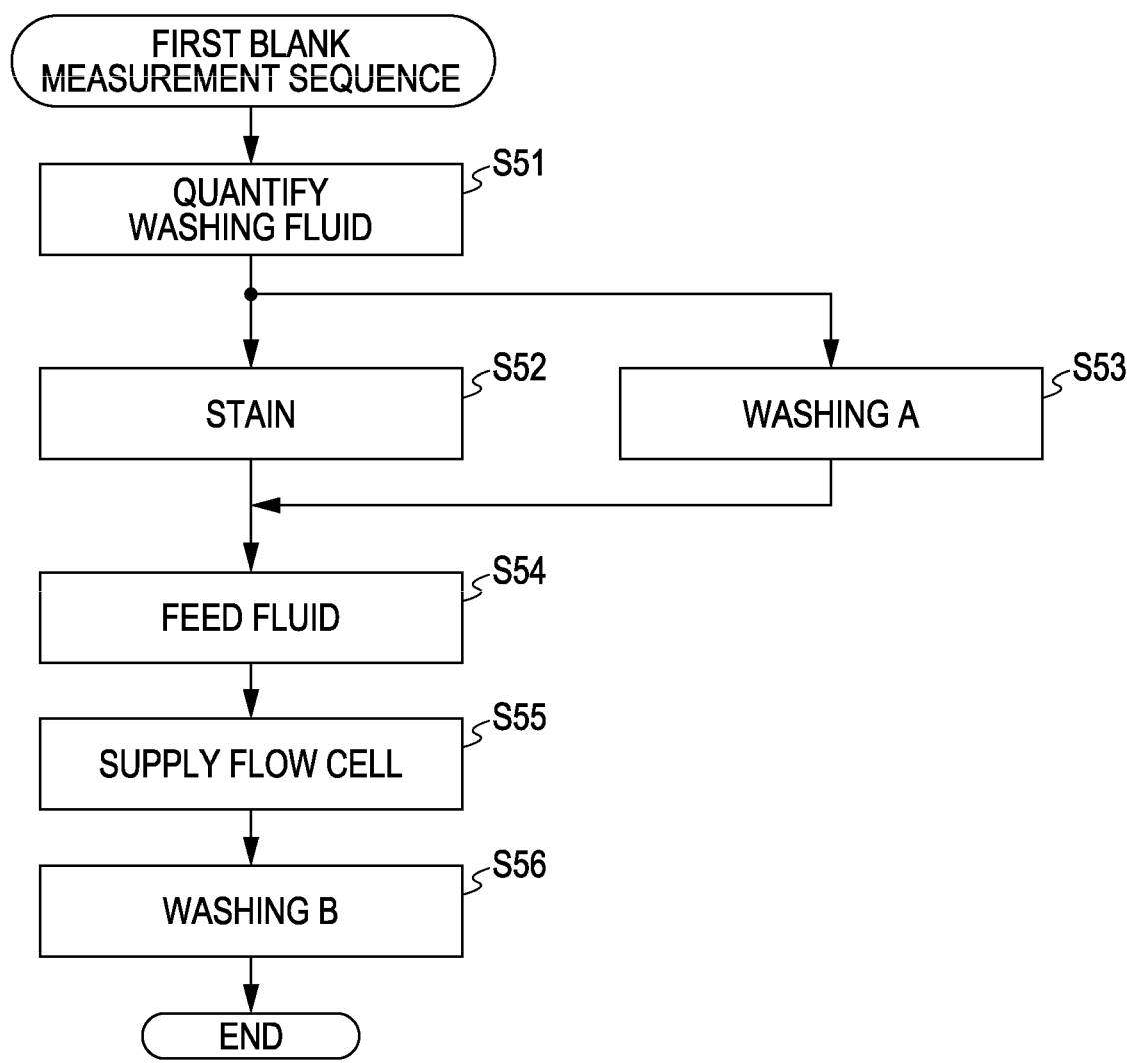
FIG. 7 is a flowchart showing a processing procedure of a first blank measurement sequence.

FIG. 7 is a flowchart showing the processing of the first blank measurement sequence. As shown in FIG. 7, the first blank measurement sequence includes steps executed in the urine measurement sequence other than the sample aspiration (step S31) and the analysis (step S37). And washing fluid is used as the sample blank in place of the sample. As shown in FIG. 4 and FIG. 7, the valves 59, 60 are first opened, the washing fluid fed from the washing fluid container 55 to the sampling valve 45 through the syringe pump 42 is quantified by the sampling valve 45, and then dispensed into the reaction chamber 48 with the diluting solution (step S51). The stain fluid is then dispensed into the reaction chamber 48, so that the washing fluid and the stain fluid are mixed by stirring the stirring blade 48a (step S52).

At the same time as the start of the staining processing of the washing fluid, the washing A for washing the flow path used in step S51 is started (step S53). This step is similar to the washing A of the sample measurement sequence (step S34), and thus the detailed description thereof will be omitted. After the washing A and the staining processing of the washing fluid are finished, the washing fluid is flown from the reaction chamber 48 to be charged between the valve 56 and the valve 57 (step S54).

The washing fluid between the valves 56, 57 is then pushed out by the syringe pump 44, and supplied from the jet nozzle 49 to the flow cell 50 (step S55). In the first blank measurement sequence, the optical detection is not carried out. The cells remaining in the flow cell 50 are thus pushed out to the outside from the flow cell 50, and the flow cell 50 is washed.

After the supplying of the washing fluid is finished, the washing B for washing the flow path used in step S54 is carried out (step S56). This step is similar to the washing B of the sample measurement sequence (step S38), and thus the detailed description thereof will be omitted.

Figure 8:
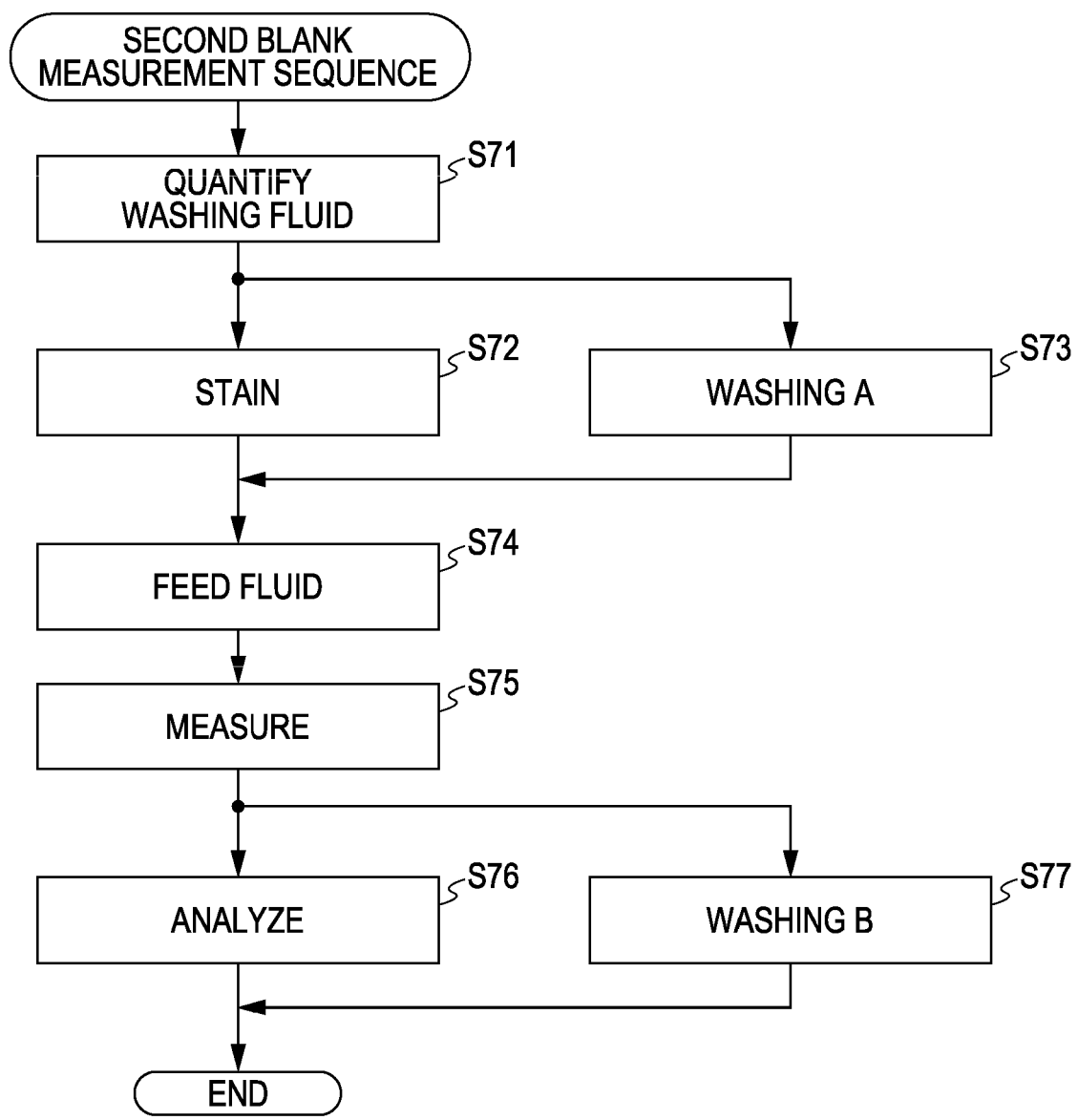
FIG. 8 is a flowchart showing a processing procedure of a second blank measurement sequence.

FIG. 8 is a flowchart showing a processing of a second blank measurement sequence. As shown in FIG. 8, the second blank measurement sequence includes steps executed in the urine measurement sequence other than the sample aspiration (step S31). And washing fluid is used as the sample blank in place of the sample. As shown in FIG. 4 and FIG. 8, similar to the first blank measurement sequence, after the washing fluid is quantified by the sampling valve 45, the washing fluid is dispensed to the reaction chamber 48 with the diluting solution (step S71), the stain fluid and the washing fluid dispensed into the reaction chamber 48 are mixed (step S72).

At the same time as the start of the staining processing of the washing fluid, the washing A of washing the sample passing flow path used in step S71 is started (step S73). This step is similar to the washing A of the urine measurement sequence (step S34), and thus the detailed description thereof will be omitted. After the washing A and the staining processing of the washing fluid are finished, the washing fluid is flown from the reaction chamber 48 to be charged between the valve 56 and the valve 57 (step S74).

The washing fluid charged between the valves 56, 57 is then measured. In this measurement, the washing fluid between the valves 56, 57 is pushed out by the syringe pump 44, and discharged from the jet nozzle 49 into the flow cell

50. The sheath fluid is pushed out at the same time as the discharging, and the sheath flow of the washing fluid formed in the flow cell 50 is irradiated with the laser light, so that the optical detector 15 detects particles contained in the washing fluid. The detected signal is then converted to an electric signal and transmitted to the system control section 13 (step S75).

In the system control section 13, the number of red blood cells, white blood cells, and bacteria flowing through the flow cell is counted (step S76) based on the electric signal, and the counting result is displayed on the display unit 72. The background which may be influenced by cells remaining in the sampling valve 45, and flow path from the reaction chamber 48 to the jet nozzle 49 thus can be measured. At the same time as the start of analysis by the system control section 13, the washing B for washing the flow path used in the steps S74, S75 in the device mechanism section 14 is started (step S77). This step is similar to the washing B of the urine measurement sequence (step S38), and thus the detailed description thereof will be omitted.

As described above, in the present embodiment, washing of flow path is carried out one time in the first mode, on the other hand, in the second mode the washing of flow path is performed three times, that is, washing operations of the body fluid measurement, the first blank measurement and the second blank measurement. And, since the sample blank used in the blank measurements is free from cells, the blank measurement also has an effect of washing of flow path. Therefore the washing carried out in the second mode can enhance effect of washing of the flow path since the amount of the washing fluid to be flown in the flow path in the second mode is greater than the amount of the washing fluid flown in the first mode. The measurement of the body fluid sample in the second mode can be carried out at high accuracy.

In the present embodiment, the amount of the washing fluid used in the second mode is set grater than that of the first mode, but the washing effect may be enhanced by changing other condition. For example, a flow speed of the washing fluid flowing through the flow path may be increased, or the direction the washing fluid flows may be reversed, the air in which the flow speed near the wall of flow path is faster than the washing fluid may be alternately flowed with the washing fluid.

Figure 9:
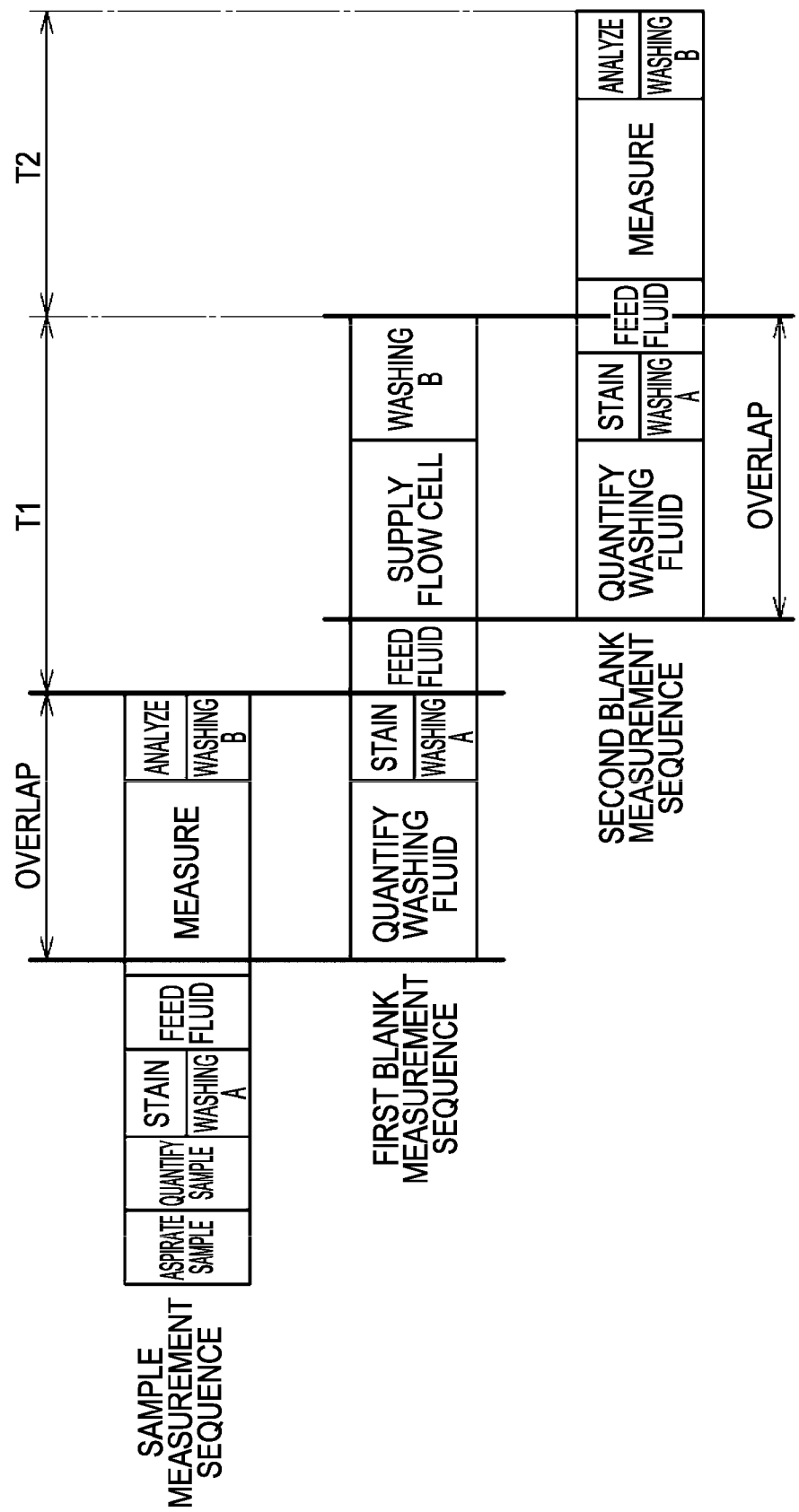
FIG. 9 is a timing chart showing a processing procedure of the sample analyzer.

FIG. 9 is a timing chart showing a processing procedure of the sample analyzer 1. As shown in FIG. 9, in the present embodiment, the processing operation of the next sequence is started during the processing operation of the previous sequence when continuously carrying out the body fluid measurement sequence, the first blank measurement sequence, and the second blank measurement sequence. In other words, in the present embodiment, the body fluid measurement sequence, the first blank measurement sequence, and the second blank measurement sequence are partly overlapped each other.

Specifically, the processing operation of quantification of the washing fluid of the first blank measurement sequence is started while the processing operation of the measurement is carried out in the body fluid measurement sequence. That is, a part of the processing operation of the body fluid measurement sequence and a part of the processing operation of the first blank measurement sequence are overlapped until the analysis and the washing B of the body fluid measurement sequence are finished. The time T1 from the end of the body fluid measurement sequence to the end of the first blank measurement sequence thus can be reduced.

The processing operation of quantification of the washing fluid of the second blank measurement sequence is started while the processing operation of the first blank measurement sequence is performed, and a part of the processing operation of the first blank measurement sequence and a part of the processing operation of the second blank measurement sequence overlap until the washing B of the first blank measurement sequence is finished. The time T2 from the end of the first blank measurement sequence to the end of the second blank measurement sequence thus can be reduced.

According to the above configuration, the time (T1+T2) from the end of the body fluid measurement sequence to the end of the second blank measurement sequence thus can be reduced.

Returning back to FIG. 5, after the second blank measurement sequence is finished in step S6, the system control section 13 determines whether or not each number of white blood cells, red blood cells, and bacteria counted by the analysis (step S76) of the second blank measurement is smaller than or equal to a threshold value (e.g., 5 cells/µL) (step S7). If each number is smaller than or equal to the threshold value, the sample analyzer 1 becomes the standby state in which the next body fluid sample can be measured (step S3). In the standby state, the message 72a shown in FIG. 10A is displayed, as described above.

Figure 10B:
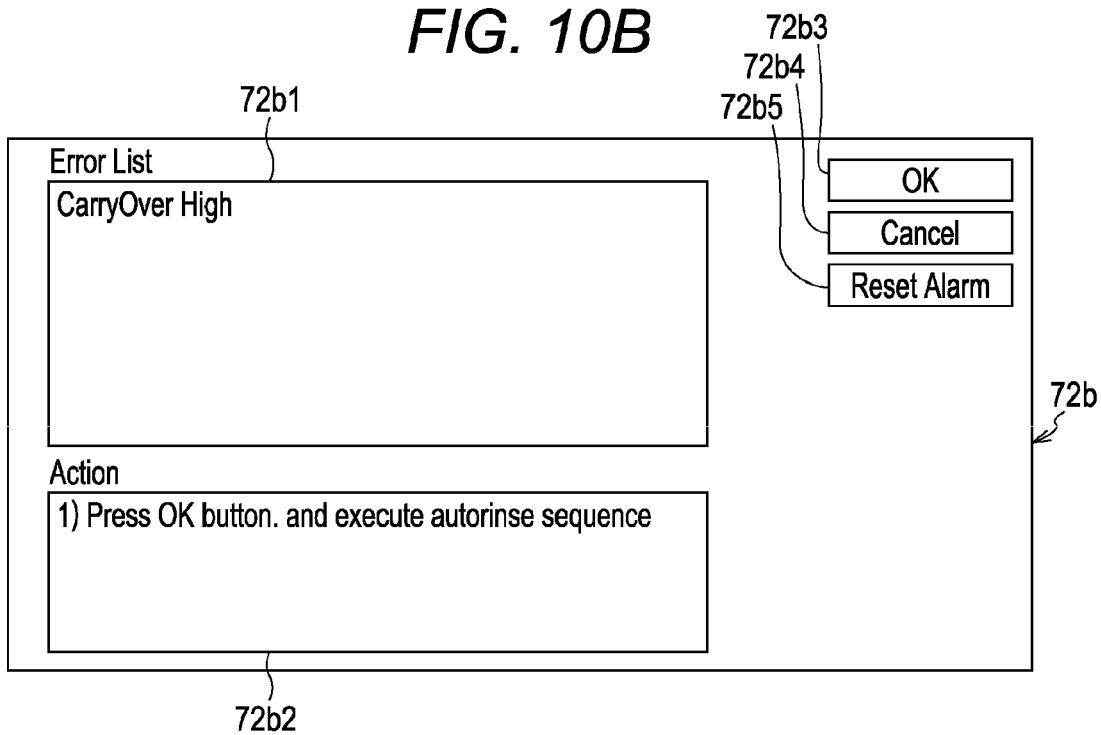
FIG. 10B is an illustrative view of an error screen displayed on the display unit.

If the result of determination in step S7 is negative, that is, if the counting result in the second blank measurement sequence is not smaller than or equal to the threshold value, an error screen 72b is displayed on the display unit 72 of the system control section 13 (step S8), as shown in FIG. 10B. If the counting result is not smaller than or equal to the threshold value, it is assumed that the washing of the flow path after a body sample is measured is not sufficient, and the possibility of carry-over is high. In the error screen 72b, the notation "Carry Over High" is displayed at the upper part 72b1 of the screen, and a message indicating that the influence of carry over may occurs in the measurement of next sample are displayed. Thus, the operator is informed that a risk of carry-over is high. Also a message urging the user to again perform the blank measurement is displayed at the lower part 72b2 of the screen. The notification of error screen 72b to inform the carry over risk is not limited to these examples. Other form of notification may be employed as long as the notification can inform the user of the risk of carry over and urge the user to again perform the blank measurement.

In the error screen 72b, when the user pushes the OK button (accepting portion) 72b3 (step S9: YES), the system control section 13 returns the processing to step S6 and again executes the blank measurement involving the washing of flow path, as shown in FIG. 5. In other words, the blank measurement performed again in the present embodiment includes performing only one time of blank measurement, so that the time required to perform the blank measurement is shorter than the time required to perform the blank measurement automatically after the measurement of the body fluid sample. The processing operation of the second blank measurement sequence in the blank measurement performed again is similar to the processing operation of the second blank measurement sequence automatically performed after the measurement of the sample, and thus the detailed description thereof will be omitted.

After the second blank measurement sequence in the blank measurement performed again is finished, the determination on whether or not the counting result is smaller than or equal to the threshold value is again performed based on the result of the measurement of the second blank measurement sequence (step S7). The sample analyzer 1 becomes the standby state (step S3) if the counting result is smaller than or equal to the threshold value. Or the error screen 72b is displayed again if the counting result is not smaller than or equal to the threshold value (step S8). Thus, in the present embodiment, the message urging the user to again perform the blank measurement is repeatedly displayed until the result of the blank measurement becomes smaller than or equal to the threshold value.

If the user pushes the cancel button 72b4 although the message urging to perform again the blank measurement is displayed in step S8, the standby state is achieved. In this case a flag indicating that the possibility of carry-over is high is given to the measurement result of the next body fluid sample. If the user pushes the reset button 72b5 in step S8, the standby state is achieved and the flag is not given to the next measurement.

According to the sample analyzer 1 of the present embodiment configured above, in the second mode, the user does not need to perform cumbersome operation to check that the cells are remaining in the flow path after the washing since the blank measurement of automatically washing the flow path used in the measurement and checking the effect of such washing is automatically carried out after the measuring section 12 measures the body fluid sample, whereby the measurement of the next body fluid sample can be smoothly started.

In the first mode, the processing ability of the urine sample does not lower since the state in which the next urine sample can be measured by the measuring section 12 is obtained after the washing of the sample passing flow path when the measuring section 12 measures the sample of urine sample, and whether or not the next sample can be measured is not determined as in the second mode.

In the second mode, the processing operation of the first blank measurement sequence involving the washing of the sample passing flow path is started while the processing operation of the sample measurement sequence is being carried out, so that a part of the processing operation of the sample measurement sequence and a part of the processing operation of the first blank measurement sequence can be carried out in parallel. The time T1 from the finishing of the sample measurement sequence to the finishing of the first blank measurement sequence thus can be reduced. As a result, the time from the finishing of the measurement of the previous body fluid sample to the start of the measurement of the next body fluid sample can be reduced, whereby the processing ability of the body fluid sample can be enhanced.

In the second mode, the processing operation of the second blank measurement sequence is started while the processing operation of the first blank measurement sequence is being carried out, so that a part of the processing operation of the first blank measurement sequence and a part of the processing operation of the second blank measurement sequence can be carried out in parallel. The time T2 from the finishing of the first blank measurement sequence to the finishing of the second blank measurement sequence thus can be reduced, and furthermore, the time (T1+T2) from the finishing of the sample measurement sequence to the finishing of the second blank measurement sequence can be reduced. As a result, the time from the finishing of the measurement of the previous body fluid sample to the start of the measurement of the next body fluid sample can be further reduced, whereby the processing ability of the body fluid sample can be enhanced.

In the second mode, if the result of determination of whether or not a state in which the measurement of the next body fluid sample can be appropriately carried out is negative, a message urging the user to again perform the blank measurement is displayed on the display unit 72 of the system control section 13, and hence the user can easily understand that the blank measurement again needs to be performed by checking the message displayed on the display unit 72.

In the second mode, the washing time is shortened when the blank measurement is performed again than in the blank measurement automatically carried out after the measurement of the sample, and hence the processing ability of the body fluid sample can be suppressed from lowering when the blank measurement is performed again.

The optical detector 15 detects a predetermined component from the sample flowing through the flow cell 50, and thus can perform such detection at high speed. The processing ability of the sample is thus further enhanced.

The washing performed in the second mode has higher washing effect than the washing performed in the first mode, and thus the result of determination performed after the washing of the second mode can be reduced from becoming negative. The operation in which the user performs the blank measurement after the measurement of the sample can be further reduced.

The present invention is not limited to the embodiment described above. For example, the sample analyzer 1 in the present embodiment measures the urine as a first type of sample in the first mode, but the blood may be measured as the first type of sample.

The sample analyzer 1 in the present embodiment can measure the urine sample and the body fluid measurement, but may measure only the body fluid sample.

Furthermore, the washing (washing A and washing B) is carried out in the sample measurement sequence of the second mode, but the washing of the sample measurement sequence does not necessarily need to be performed if sufficient washing can be performed with the washing of the blank measurement.

In the embodiment described above, a configuration of automatically executing the blank measurement before measuring the next body fluid sample after measuring one body fluid sample has been described, but a configuration of automatically executing the blank measurement before the measurement of the body fluid sample measured first may be adopted. For example, the processing of steps S5 to S9 may be executed when changed from the first mode to the second mode.

The blank measurement in the second mode is performed for a total of two times, the first blank measurement and the second blank measurement, but at least one blank measurement may be carried out. For example, when performing the blank measurement only once, the second blank measurement sequence is performed once without performing the first blank measurement sequence. When performing the blank measurement three or more times, the first blank measurement sequence is repeated two or more times, and then the second blank measurement sequence is performed once. When performing the blank measurement for a predetermined number of times (plural times), the washing fluid in the washing fluid container 55 may become insufficient. If the washing fluid becomes insufficient before reaching the predetermined number of times, the processing automatically may transition to the determination step.

In the present embodiment, the urine measurement sequence in the first mode and the body fluid measurement sequence in the second mode are executed in the same step, but may be different sequences. For example, the body fluid has less number of contained cells, that is, low cell concentration compared to the urine. When measuring the body fluid, whether or not a small amount of cells contained in the body fluid can be detected affects the accuracy of the measurement. When measuring the body fluid, therefore, the amount of specimen to use for the measurement may be increased than when measuring the urine to enhance the measurement accuracy. Specifically, the amount of specimen flowing in the flow cell 50 in the body fluid measurement sequence is made greater (e.g., three times) than that in the urine measurement sequence. In this case, the measurement time in the body fluid measurement sequence becomes lower than the measurement time in the urine measurement sequence since the flow rate of the specimen flow to the flow cell is constant.

In the present embodiment, in the second mode, the sample measurement sequence and the first blank measurement sequence are overlapped and the first blank measurement sequence and the second blank measurement sequence are overlapped, but only one of which may be overlapped. Such overlapping does not necessarily need to be carried out. In this case, the washing in the sample measurement sequence may be collectively carried out after the measurement is finished without performing it two times (washing A and washing B) in the first half and the second half.

In the present embodiment, whether or not the number of detected cells is smaller than or equal to a threshold value may be determined after automatically performing the blank measurement, the device is transitioned to the standby state if the number of detected cells is smaller than or equal to the threshold value, and a message indicating that the possibility of carry-over is high is output if the number of detected cells is greater than the threshold value, but the number of detected cells may be displayed.

In the present embodiment, the automatic blank measurement is not performed after the washing in the first mode, but the blank measurement may be automatically performed in the first mode as well.

The urine barely contains cells if collected from a healthy person, and thus the threshold value used for the determination normal/abnormal is set low compared to the blood. Thus, the influence of the carry-over on the measurement result is also large in the urine sample.

The urine sample thus can be more accurately measured by automatically performing the blank measurement after the washing for the urine sample as well.

In the present embodiment, an example of performing the automatic blank measurement after the washing in the mode for measuring the body fluid has been described, but the present invention can be suitably applied to a case of measuring a small amount of sample such as the blood of a child for the sample.

When measuring a small amount of sample, the sample is diluted at a dilution magnification higher than the normal sample and then measured, and the measured result is converted to the concentration before the dilution. Thus, when the carry-over occurs, the carry-over greatly influences the final measurement result.

In the sample analyzer capable of setting small amount sample mode for measuring the small amount of sample, the blank measurement is automatically carried out after the washing of the sample to more accurately measure the small amount of sample.

As a more specific example, the sample analyzer is configured as below. In other words, the sample analyzer is configured to selectively set the small amount sample mode for measuring the small amount of sample, and the normal sample mode for measuring the normal sample. In this example, the normal sample mode corresponds to the first mode of the embodiment described above, and the small amount sample mode corresponds to the second mode.

The sample analyzer is configured to aspirate the sample, dilute the aspirated sample with the diluting solution, and feeding the diluted sample to the detecting section through the flow path to measure the sample. The sample analyzer aspirates the sample of a less amount if the small amount sample mode is set than when the normal sample mode is set, and dilutes the sample at the dilution magnification of the same amount as or greater amount than when the normal sample mode is set. Thus, the small amount of sample is thereby diluted at the dilution magnification higher than when the normal sample mode is set.

The sample analyzer performs the washing after the measurement of the sample and transitions to the standby state if the normal sample mode is set. The sample analyzer performs the washing after the measurement of the sample, and then automatically performs the blank measurement if the small amount sample mode is set. An example of the sample analyzer including the small amount sample mode includes a device described in Japanese Unexamined Patent Publication No. 2009-36530.

An example in which the sample analyzer automatically dilutes the sample at high magnification has been described for the small amount sample mode, but instead, a dilution measurement mode of measuring a sample, which is manually diluted at high magnification in advance by the user, may be set.

What is claimed is:
1. A sample analyzer comprising:
a sample measuring section including a reaction chamber for preparing a measurement sample from a biological specimen and a stain fluid, a detecting section for detecting a component contained in the measurement sample and a flow path for feeding the measurement sample to the detecting section; and
a control section comprising a processor configured with a program to perform operations comprising controlling the sample measuring section to prepare the measurement sample in the reaction chamber, to feed the prepared measurement sample to the detecting section through the flow path, to detect the component contained in the measurement sample with the detecting section, and then to control the sample measuring section to automatically flow washing fluid to the flow path, the reaction chamber and the detection section to perform washing of the flow path, the reaction chamber and the detection section, wherein
the measurement sample comprises cerebrospinal fluid, pleural effusion, ascetic fluid, pericardial fluid, joint fluid, peritoneal dialysis fluid or intra-abdominal washing fluid, and
the processor of the control section is configured with the program to perform operations further comprising:
while the sample measuring section is performing the washing, automatically controlling the sample measuring section to start preparing a blank measurement sample in the reaction chamber from a blank sample having no cells in the blank sample and the stain fluid, and
then feeding the prepared blank measurement sample to the detecting section through the flow path and detecting a component contained in the prepared blank measurement sample to check a sufficiency of the washing.

2. The sample analyzer according to claim 1, wherein the sample measuring section starts the washing of the flow path used to feed the fluid to the detecting section while the detecting section is performing the detection for the measurement sample or the blank measurement sample.

3. The sample analyzer according to claim 1, wherein after the sample measuring section completes the washing of the flow path, the processor of the control section is configured with the program to perform operations to cause the sample measuring section to continuously perform measurements of a blank measurement sample for checking the background over plural times, and the sample measuring section starts to prepare the second blank measurement sample while the first blank measurement sample is flowing through the detecting section.

4. The sample analyzer according to claim 1, wherein the processor of the control section is configured with the program to perform operations to determine whether or not the washing is sufficient enough to suppress carry-over based on a result of detection of the component contained in the blank measurement sample.

5. The sample analyzer according to claim 4, further comprising a display unit, wherein the processor of the control section is configured with the program to perform operations to display on the display unit a screen including an alert to urge a user to again perform the measurement of the blank measurement sample when determining that the washing is insufficient.

6. The sample analyzer according to claim 5, wherein the screen further includes a button for accepting an instruction to again perform the measurement of the blank measurement sample.

7. The sample analyzer according to claim 6, wherein the processor of the control section is configured with the program to perform operations to cause the sample measuring section to again execute the measurement of the blank measurement sample when the button is operated.

8. The sample analyzer according to claim 6, further comprising a cancel button to cancel the alert, wherein when the cancel button is operated, the processor of the control section is configured with the program to perform operations to cancel the alert, and the sample measuring section transitions to a state in which the measurement of a next measurement sample can be started.

9. The sample analyzer according to claim 8, wherein when the cancel button is operated and the next measurement sample is measured, the processor of the control section is configured with the program to perform operations to output the measurement result of the next measurement sample added with a flag indicating that the carry-over risk is high.

10. The sample analyzer according to claim 1, further comprising a display unit, wherein the processor of the control section is configured with the program to perform operations to display on the display unit a screen including an alert to urge a user to again perform the measurement of the blank measurement sample when a number of cells detected from the blank measurement sample exceeds a threshold value.

11. The sample analyzer according to claim 1, wherein the sample measuring section includes a washing fluid container containing washing fluid, and the washing fluid contained in the washing fluid container is used as the blank measurement sample.

12. The sample analyzer according to claim 1, the detecting section includes a flow cell, a light source for irradiating light on a specimen flowing through the flow cell, and a light receiving section for receiving light emitted from particles in the specimen.

13. A sample analyzer comprising:
a sample measuring section including a reaction chamber for preparing a measurement sample from a biological specimen and a stain fluid, a flow path for feeding the measurement sample, and a detecting section for detecting a component contained in the measurement sample fed through the flow path; and
a control section comprising a processor configured with a program to perform operations comprising:
controlling the sample measuring section based on a mode selected from a first mode for measuring a first type of sample and a second mode for measuring a second type of sample, wherein for the first mode and the second mode, the processor of the control section is configured with the program to perform operations to control the sample measuring section to prepare the measurement sample in the reaction chamber, to feed the measurement sample from the flow path toward the detecting section and to detect the component contained in the measurement sample with the detecting section, and thereafter, control the sample measuring section to automatically flow washing fluid to the flow path, the reaction chamber and the detection section to perform washing of the flow path the reaction chamber and the detection section, wherein
the second type of sample is cerebrospinal fluid, pleural effusion, ascetic fluid, pericardial fluid, joint fluid, peritoneal dialysis fluid or intra-abdominal washing fluid,
for the second mode, the processor of the control section is configured with the program to perform operations comprising:
while the sample measuring section is performing the washing, automatically control the sample measuring section to start preparing a blank measurement sample in the reaction chamber from a blank sample having no cells in the blank sample and the stain fluid, and
then feeding the prepared blank measurement sample to the detecting section through the flow path and detecting a component contained in the prepared blank measurement sample to perform a background check for checking effect of the washing, and
for the first mode, the processor of the control section is configured with the program to perform operations comprising permitting the measurement of a next measurement sample by skipping the background check.

14. The sample analyzer according to claim 13, wherein the processor of the control section is configured with the program to perform operations comprising prohibiting the measurement of the next measurement sample if a number of particles detected by the background check of the blank measurement sample exceeds a predetermined threshold value, and permits the measurement of the next measurement sample if the number of particles detected by the background check is smaller than the predetermined threshold value.

15. The sample analyzer according to claim 14, the detecting section includes a flow cell, a light source for irradiating light on a specimen flowing through the flow cell, and a light receiving section for receiving light emitted from particles in the specimen.

16. The sample analyzer according to claim 15, wherein when the second mode is set, the processor of the control section is configured with the program to perform operations comprising causing the sample measuring section to flow to the flow cell an amount greater than that flown to the flow cell when the first mode is set.

17. The sample analyzer according to claim 15, wherein when the second mode is set, the processor of the control section is configured with the program to perform operations comprising causing the sample measuring section to flow the measurement sample to the flow cell over a time longer than a time of flowing the measurement sample to the flow cell when the first mode is set.

18. The sample analyzer according to claim 13, further comprising an operation receiver that receives an operation by a user to select the mode from the first and second modes.

\* \* \* \* \*